US00PP14258P29

(12) United States Plant Patent
Hanes

(10) Patent No.: US PP14,258 P2
(45) Date of Patent: Oct. 28, 2003

(54) PETUNIA PLANT NAMED 'WHIP BURG'

(50) Latin Name: *Petunia hybrida*
Varietal Denomination: Whip Burg

(75) Inventor: Mitchell Eugene Hanes, Morgan Hill, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 10/389,060

(22) Filed: Mar. 13, 2003

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates P.C.

(57) ABSTRACT

A petunia cultivar particularly distinguished by burgundy colored flowers, compact habit and good basal branching.

1 Drawing Sheet

Genus and species: Petunia hybrida.
Variety denomination: 'Whip Burg'.

BACKGROUND OF THE NEW PLANT

The present invention comprises a new and distinct cultivar of petunia, botanically knowvn as Petunia hybrida, and hereinafter referred to by the cultivar name 'Whip Burg'. The new cultivar is asexually reproduced from vegetative cuttings and tissue culture resulting from the cross of the seed/pod parent 99-189-1, a red proprietary line that is unnamed and unpatented×99-1-4, a purple proprietary line that is unnamed and unpatented.

'Whip Burg' is a product of a planned breeding program intended to create new petunia plants with burgundy colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Whip Burg'. The data, which defines these characteristics, were collected from asexual reproductions carried out in Gilroy, Calif. The plant history was taken on 5 month old plants grown in one-gallon pots in fall/winter season, in a poly-covered greenhouse under 2–4 hours supplemental light and color readings were taken in the greenhouse in the winter season under natural light. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Petunia hybrida.
*Commercial.*—Petunia.
Form: Semi upright, but more decumbent.
Growth and branching habit: Good vigorous habit, well-branched, full plant.
Height: From soil level to top of blooms: Approximately 5–10 cm.
Width: Approximately 30–40 cm including flowers.
Time to produce a finished flowering plant: 9–11 weeks.
Outdoor plant performance: Full sun; free flowering through the summer; some heat tolerance; Used as a hanging plant, in mixed container plantings, and mass planting in a bed.
Time to initiate roots: Approximately 18–23 days in the greenhouse.
Root description: Fibrous, white.

THE LEAVES

Arrangement: Alternate, upper leaves sub-opposite.
Length: 3.9–5.5 cm.
Width: 3.9–4.2 cm.
Leaf blade shape: Ovate.
Leaf margin: Entire.
Apex aspect: Rounded.
Base aspect: Acuminate.
Leaf color: Upper side; RHS 137A (green); Underside; RHS 138A (green).
Texture: Verrucose only, no glandular hairs.
Venation: Palmate.
Venation color: RHS 144B (yellow-green).
Petiole length: 0.7–1.7 cm.
Petiole width: 0.25–0.3 cm.
Petiole color: RHS 144B/C (yellow-green).
Petiole texture: Smooth and very few, long glandular hairs.

THE STEM

Length: 40–45 cm.
Diameter: 0.3–0.4 cm.
Internode length: 1.0–2.5 cm.
Color: RHS 144A (yellow-green).
Texture: Smooth and very few, long glandular hairs.
Stem anthocyanin: Yes, reddish, very irregular, heavy in some areas and light to none in other areas.
Peduncle color: RHS 144B (yellow-green).
Peduncle length: 1.7–3.3 cm.
Peduncle diameter: 0.15 cm.
Peduncle texture: Many glandular hairs.

THE BUD

Shape: Oblong.
Diameter: 0.4 cm.
Length: 1.0–3.2 cm.
Color at tight bud: RHS N79A (purple).

THE FLOWER

Blooming habit: Continuous all through the growing season. Good floriferousness.
Inflorescence type: Flowers solitary in upper leaf axis.
Young flower color: Closest to RHS 61A (red-purple) but more blue-purple under tones; RHS N77A (purple) mid-veins; very faint RHS N77A (purple) secondary veining.
Mature flower color: Upper side, closest to RHS 61A (red-purple), but more blue-purple under tones; RHS N77A (purple) mid-veins, very faint RHS N77A (purple) secondary veining. Underside, between RHS 72A (red-purple); RHS N77A (purple) mid-veins; lighter shade of RHS N77A (purple) in moderate amount, secondary veining.
Corolla tube colors inside: Closest to RHS 61A (red-purple), but more blue-purple under tones; RHS N77A (purple) mid-veins, faint but heavy in quantity RHS N77A (purple) secondary veining.
Corolla tube length: 1.8–2.0 cm.
Corolla outside texture: Glandular hairs.
Floret form and number of petals: Funnel form, 5 lobed petals fused at base.
Flower (limb) diameter: 3.5–3.7 cm.
Petal apex shape: Praemorse.
Petal base shape: Fused.
Petal margin: Entire.
Waviness of petals: Weak.
Petal lobation: Weak.
Petal texture: Papillose; very velvety.
Sepals: 5, fused at the base.
Sepal color: RHS 137C (green).
Sepal length: 1.8–1.9 cm.
Sepal width: 0.4–0.7 cm.
Sepal shape: Oblong.
Sepal apex: Acute to Obtuse.
Sepal texture: Many glandular hairs.
Lastingness of individual blooms: 4–8 days.
Fragrance: None.

THE REPRODUCTIVE ORGANS

Stamens: 5; 2 taller, 2 short, 1 much shorter.
Filament color: RHS N155B (white).
Pollen color: RHS 201C (grey).
Pistil: One.
Stigma: RHS 144A (yellow-green).
Style color: Bottom half, between RHS 144C/D (yellow-green); top half, lighter than RHS N79B (purple) with a blotch of RHS N79A (purple) under the stigma.
Fruit seed set: Not observed.

DISEASE AND INSECT RESISTANCE

Not observed.

COMPARISON WITH KNOWN CULTIVARS

Compared to its female parent 99-189-1 in the following ways: The female parent is an upright growing, late flowering, and red flower plant. The hybrid is an earlier flowering small flowered burgundy plant.

Compared to its male parent 99-1-4 in the following ways: The male parent is a late flowering, trailing plant with purple flowers. The hybrid is an earlier flowering; more free flowering plant with burgundy flowers.

I claim:

1. A new and distinct petunia plant as shown and described herein.

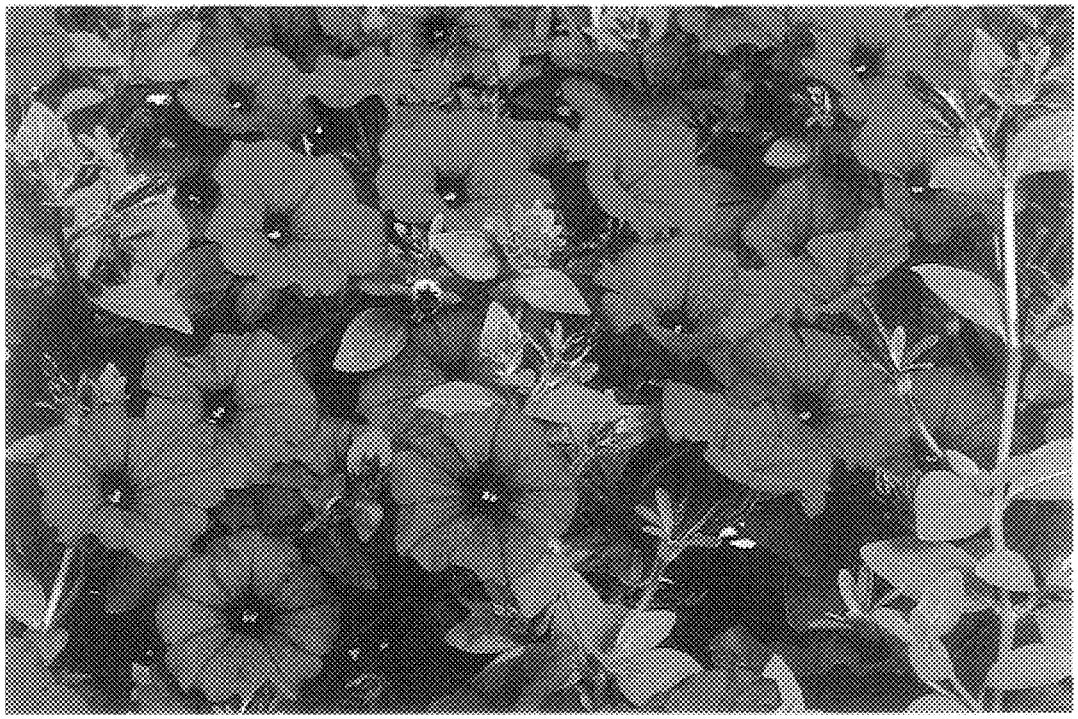

* * * * *